(12) United States Patent
Perryman et al.

(10) Patent No.: US 6,759,048 B1
(45) Date of Patent: Jul. 6, 2004

(54) **NEUTRALIZATION-SENSITIVE EPITOPES OF *CRYPTOSPORIDIUM PARVUM***

(75) Inventors: Lance E. Perryman, Cary, NC (US); Douglas P. Jasmer, Albion, WA (US); Michael W. Riggs, Tucson, AZ (US); Travis C. McGuire, Pullman, WA (US)

(73) Assignees: North Carolina State University, Raleigh, NC (US); Arizona Board of Regents, Tucson, AZ (US); Washington State University Regents, Pullman, WA (US)

( * ) Notice: Subject to any disclaimer, the term of this patent is extended or adjusted under 35 U.S.C. 154(b) by 0 days.

(21) Appl. No.: 09/949,186

(22) Filed: Sep. 6, 2001

Related U.S. Application Data

(62) Division of application No. 08/916,246, filed on Aug. 22, 1997, now Pat. No. 6,323,020.
(60) Provisional application No. 60/023,440, filed on Aug. 23, 1996.

(51) Int. Cl.$^7$ ...................... A61K 39/00; A61K 39/002; A61K 38/00; C07K 14/00; C07K 1/00
(52) U.S. Cl. ................................ 424/185.1; 424/191.1; 424/265.1; 424/266.1; 530/300; 530/324; 530/329; 530/350
(58) Field of Search .......................... 424/184.1, 185.1, 424/191.1, 265.1, 266.1; 530/300, 350, 324, 329

(56) References Cited

U.S. PATENT DOCUMENTS

| | | | |
|---|---|---|---|
| 4,708,871 A | 11/1987 | Geysen | |
| 5,302,527 A | 4/1994 | Birkett et al. | |
| 6,015,882 A | 1/2000 | Petersen et al. | |
| 2001/0028882 A1 | 10/2001 | Riggs et al. | |

FOREIGN PATENT DOCUMENTS

| | | |
|---|---|---|
| WO | WO 90/11092 | 10/1990 |
| WO | WO 93/24649 | 12/1993 |

OTHER PUBLICATIONS

Harp et al (J. of Diary Science vol. 81 No. 1, pp 289–294), Jan. 1998.*

Perryman et al. "A Cloned Gene of *Cryptosporidium parvum* Encodes Neutralization–Sensitive Epitopes." *Molecular and Biochemical Parasitology*, vol. 80, pp. 137–147 (1996).

Riggs, M.W. "Immunology: Host Response and Development of Passive Immunotherapy and Vaccines." *Cryptosporidium and Cryptosporidiosis*, CRC Press (1997).

Jenkins et al. "Serum and Colostrum Antibody Responses Induced by Jet–Injection of Sheep with DNA Encoding a *Cryptosporidium parvum* Antigen," *Vaccine*, vol. 13, Issue 17, pp. 1658–1664 (1995).

Stryer, *Biochemistry*. 3$^{rd}$ edition, p. 72. 1988.

Arrowood et al.; *Effects of Immune Colostrum and Orally Administered Antisporozoite MonoclonalAntibodies on the Outcome of Cryptosporidium parvum Infections in Neonatal Mice*, Infection and Immunity 57:8 2283–2288 (Aug. 1989).

Arrowood et al.; *Immunofluorescent Microscopical Visualization of Trails Left by Gliding Cryptosporidium parvum Sporozoites*, J. Parasitol. 77:2 315–317 (1991).

Riggs et al.; *Neutralization–Sensitive Epitopes are Exposed on the Surface of Infectious Cryptosporidium parvum Sporozoites*, The Journal of Immunology 143:4 1340–1345 (Aug. 15, 1989).

Tilley et al.; *Identification of a 15–Kilodalton Surface Glycoprotein on Sporozoites of Cryptosporidium parvum*, Infection and Immunity 59:3 1002–1007 (Mar. 1991).

Peterson et al., *Identification and Initial Characterization of Five Cryptosporidium parvum Sporozoite Antigen Genes*, Infection and Immunity 60(6): 2343–2348 (Jun. 1992).

Baehr et al.; "The virulence–associated gonococcal H.8 gene encodes 14 tandemly repeated pentapeptides," *Molecular Microbiology* 3:1 49–55 (1989).

Woods et al.; "Conserved lipoprotein H.8 of pathogenic *Neisseria* consists entirely of pentapeptide repeats," *Molecular Microbiology* 3:1 43–48 (1989).

Mead et al., "Antigens of *Cryptosporidium* sporozoites Recognized by Immune Sera of Infected Animals and Humans," *J. Parasit.* 74(1): 135–143 (1988).

Perryman et al., "Kinetics of *Cryptosporidium parvum* Sporozoite Neutralization by Monoclonal Antibodies, Immune Bovine Serum, and Immune Bovine Colostrum," *Infection and Immunity* 58 (1): 257–259 (1990).

Riggs et al., "Bovine Antibody against *Cryptosporidium parvum* Elicits a Circumsporozoite Precipitate–Like Reaction and Has Immunotherapeutic Effect against Persistent Cryptosporidiosis in SCID Mice," *Infection and Immunity* 62(5): 1927–1939 (1994).

Bonnin et al. "Characterization of Microneme Antigens of *Cryptosporidium Parvum*(Protozoa, Apicomplex) "*Infection and Immunity* 59(5): 1703–1708 (May 1991).

Cho, Myung–Hwan "Passive Transfer of Immunity Against Cryptosporidium Infection in Neonatal Mice Using Monoclonal Antibodies" *Korean Journal of Parasitology* 31(3):223–230 (Sep. 1993).

(List continued on next page.)

*Primary Examiner*—Mark Navarro
(74) *Attorney, Agent, or Firm*—Myers Bigel Sibley & Sajovec P.A.

(57) ABSTRACT

DNA sequences encoding epitopes to which sporozoite-neutralizing antibodies are directed are provided. Recombinant proteins and synthetic peptides containing *Cryptosporidium parvum* epitopes for inducing an antigenic response are described.

16 Claims, 5 Drawing Sheets

OTHER PUBLICATIONS

Peterson et al., "Characterization of a >900,000–M *Cryptosporidium parvum* Sporozoite Glycoprotein Recognized by Protective Hyperimmune Bovine Colostral Immunoglobulin" *Infection and Immunity* 60(12):5132–5138 (Dec. 1992).

Priest et al. "Detection by Enzyme Immunoassay of Serum Immunoglobulin G Antibodies that Recognize Specific *Cryptosporidium parvum* Antigens" *Journal of Clinical Microbiology* 37(5):1385–1392 (May 1999).

Riggs et al. "Anti–*Cryptosporidium Parvum* Preparations" U.S. Application Serial No. 09/557,324.

Riggs et al. "Molecular Targets for Passive Immunothereay of Cryptosporidiosis"3$^{rd}$International Workshop on Opportunistic Protozoan Pathogens, Cleveland, Ohio (Jun. 1994) (Abstract).

Riggs et al. "Protective Monoclonal Antibody Defines a Circumsporozoite–Like Glycoprotein Exoantigen of *Cryptosporidium Parvum* Sporozoites and Merozoites" *Journal of Immunology* 158:1787–1795 (1997).

Ungar et al. "Cessation of *Crytosporidium*–Associated Diarrhea in an Acquired Immunodeficiency Syndrome Patient After Treatment with Hyperimmune Bovine Colostrum" *Gastroenterology*98:486–489 (1990).

Watzl et al. "Enhancemment of Resistance to *Cryptosporidium parvum* by Pooled Bovine Colostrum During Murine Retroviral Infection"*Am. J. Trop. Med. Hyg.* 48(4):519–523 (1993).

* cited by examiner

1   MGCSSSKPETKVAENKSAADANKQRELAEKKAQLAKAVKMPAPISNQAQQ

51  KPEEPKKSEPAPNNPPAADAPAAQAPAAPAEPAPQDKPADAPAAEAPAAE

101 PAAQQDKPADA

1    CAAAGAAAAAGTGAATAACAAATCATTATTTATTTACTTTGAAAAATTAT

51   TTTTACGTTCCTTCCACTTGAAAGAAAAAGTATTTTTAGTTTTATTATTC

101  AATATTAAAAATGGGTTGTTCATCATCAAAGCCAGAAACTAAAGTTGCTG
              M  G  C  S  S  S  K  P  E  T  K  V  A  E

151  AAAATAAATCTGCAGCAGATGCTAACAAACAAAGAGAATTAGCTGAAAAG
      N  K  S  A  A  D  A  N  K  Q  R  E  L  A  E  K

201  AAGGCTCAATTAGCCAAGGCTGTAAAGAATCCAGCTCCAATCAGCAACCA
      K  A  Q  L  A  K  A  V  K  N  P  A  P  I  S  N  Q

251  AGCTCAACAAAAGCCAGAAGAACCAAAGAAGTCCGAGCCTGCTCCCAATA
      A  Q  Q  K  P  E  E  P  K  K  S  E  P  A  P  N  N
                                         ↑

301  ATCCTCCAGCTGCTGATGCACCAGCAGCCCAAGCTCCTGCTGCCCTGCT
       P  P  A  A  D  A  P  A  A  Q  A  P  A  A  P  A

351  GAACCTGCTCCACAGGATAAGCCAGCTGATGCCCCAGCTGCTGAAGCTCC
      E  P  A  P  Q  D  K  P  A  D  A  P  A  A  E  A  P

401  AGCTGCTGAACCTGCTGCTCAACAAGACAAGCCAGCTGATGCCTAAATTA
      A  A  E  P  A  A  Q  Q  D  K  P  A  D  A

451  TTGTTAAAAAATGCCTTAGCAGTTGTACACTCAGAGAGTACTTAACATGG

501  GTTGAACTTTTCACAATTGAAAAATTAAACTGGGAGTTCCCTTGTATACT

551  TTAATACCAATAATAATAACAATAGAGTGTTTTTTATTAAGGTTGTTAAT

601  CTAAAAAAAAAAAAAAAAA

FIG. 3B

SEQUENCE LISTING

<160> NUMBER OF SEQ ID NOS: 12

<210> SEQ ID NO 1
<211> LENGTH: 602
<212> TYPE: DNA
<213> ORGANISM: Cryptosporidium parvum
<220> FEATURE:
<221> NAME/KEY: CDS
<222> LOCATION: (111)..(443)
<223> OTHER INFORMATION:

<400> SEQUENCE: 1

```
caaagaaaaa gtgaataaca aatcattatt tatttactttt gaaaaattat ttttacgttc      60
cttccacttg aaagaaaaag tatttttagt tttattattc aatattaaaa atg ggt         116
                                                          Met Gly
                                                            1 tgt tca tca tca aag cca gaa act aaa gtt gct gaa aat aaa tct gca        164
Cys Ser Ser Ser Lys Pro Glu Thr Lys Val Ala Glu Asn Lys Ser Ala
          5                  10                  15 gca gat gct aac aaa caa aga gaa tta gct gaa aag aag gct caa tta       212
Ala Asp Ala Asn Lys Gln Arg Glu Leu Ala Glu Lys Lys Ala Gln Leu
     20                  25                  30
```

-continued

```
gcc aag gct gta aag aat cca gct cca atc agc aac caa gct caa caa    260
Ala Lys Ala Val Lys Asn Pro Ala Pro Ile Ser Asn Gln Ala Gln Gln
 35              40                  45                  50 aag cca gaa gaa cca aag aag tcc gag cct gct ccc aat aat cct cca    308
Lys Pro Glu Glu Pro Lys Lys Ser Glu Pro Ala Pro Asn Asn Pro Pro
             55                  60                  65 gct gct gat gca cca gca gcc caa gct cct gct gcc cct gct gaa cct    356
Ala Ala Asp Ala Pro Ala Ala Gln Ala Pro Ala Ala Pro Ala Glu Pro
         70                  75                  80 gct cca cag gat aag cca gct gat gcc cca gct gct gaa gct cca gct    404
Ala Pro Gln Asp Lys Pro Ala Asp Ala Pro Ala Ala Glu Ala Pro Ala
     85                  90                  95 gct gaa cct gct gct caa caa gac aag cca gct gat gcc taaattattg     453
Ala Glu Pro Ala Ala Gln Gln Asp Lys Pro Ala Asp Ala
100                 105                 110 ttaaaaaatg ccttagcagt tgtacactca gagagtactt aacatgggtt gaacttttca   513
caattgaaaa attaaactgg gagttccctt gtatacttta ataccaataa taataacaat   573
agagtgtttt ttattaaggt tgttaatct                                    602
```

```
<210> SEQ ID NO 2
<211> LENGTH: 111
<212> TYPE: PRT
<213> ORGANISM: Cryptosporidium parvum

<400> SEQUENCE: 2

Met Gly Cys Ser Ser Lys Pro Glu Thr Lys Val Ala Glu Asn Lys
1               5                   10                  15

Ser Ala Ala Asp Ala Asn Lys Gln Arg Glu Leu Ala Glu Lys Lys Ala
                20                  25                  30

Gln Leu Ala Lys Ala Val Lys Asn Pro Ala Pro Ile Ser Asn Gln Ala
            35                  40                  45

Gln Gln Lys Pro Glu Glu Pro Lys Lys Ser Glu Pro Ala Pro Asn Asn
        50                  55                  60

Pro Pro Ala Ala Asp Ala Pro Ala Ala Gln Ala Pro Ala Ala Pro Ala
65                  70                  75                  80

Glu Pro Ala Pro Gln Asp Lys Pro Ala Asp Ala Pro Ala Ala Glu Ala
                85                  90                  95

Pro Ala Ala Glu Pro Ala Ala Gln Gln Asp Lys Pro Ala Asp Ala
            100                 105                 110

<210> SEQ ID NO 3
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 3

Cys Leu Ala Pro Gln Asp Lys Pro Ala Asp Ala Pro Ala Ala Glu Ala
1               5                   10                  15

Pro Ala Ala Glu Pro Ala Ala Gln Gln Asp Lys Pro Ala Asp Ala
            20                  25                  30

<210> SEQ ID NO 4
<211> LENGTH: 27
<212> TYPE: PRT
<213> ORGANISM: Artificial Sequence
<220> FEATURE:
<223> OTHER INFORMATION: Synthetic Peptide
```

-continued

```
<400> SEQUENCE: 4

Gln Asp Lys Pro Ala Asp Ala Pro Ala Ala Glu Ala Pro Ala Ala Glu
1               5                   10                  15

Pro Ala Ala Gln Gln Asp Lys Pro Ala Asp Ala
            20                  25

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Lys Glu Ser Gln Ala Tyr Tyr Asp Gly Arg Arg Ser Ser Ala Val Leu
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Glu Pro Ala Ala Gln Gln Asp Lys Pro Ala Asp Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Ala Ala Glu Ala Pro Ala Ala Glu Pro Ala Ala Gln
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Gln Asp Lys Pro Ala Asp Ala Pro Ala Ala Glu Ala
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 9

Gln Asp Lys Pro Ala Asp
1               5

<210> SEQ ID NO 10
<211> LENGTH: 4
<212> TYPE: PRT
<213> ORGANISM: Artificial Sequence
<220> FEATURE:
```

```
<223> OTHER INFORMATION: Synthetic Peptide
<221> NAME/KEY: MISC_FEATURE
<222> LOCATION: (4)..(4)
<223> OTHER INFORMATION: "Xaa" represents any amino acid.

<400> SEQUENCE: 10

Pro Ala Ala Xaa
1

<210> SEQ ID NO 11
<211> LENGTH: 49
<212> TYPE: PRT
<213> ORGANISM: Cryptosporidium parvum

<400> SEQUENCE: 11

Asn Asn Pro Pro Ala Ala Asp Ala Pro Ala Ala Gln Ala Pro Ala Ala
1               5                   10                  15

Pro Ala Glu Pro Ala Pro Gln Asp Lys Pro Ala Asp Ala Pro Ala Ala
            20                  25                  30

Glu Ala Pro Ala Ala Glu Pro Ala Ala Gln Gln Asp Lys Pro Ala Asp
        35                  40                  45

Ala

<210> SEQ ID NO 12
<211> LENGTH: 187
<212> TYPE: PRT
<213> ORGANISM: Artificial Sequence
<220> FEATURE:
<223> OTHER INFORMATION: Recombinant C7 Protein

<400> SEQUENCE: 12

Leu Glu Phe Ser Leu Val Leu Tyr Ser Ser Val Thr Thr Pro Leu Ile
1               5                   10                  15

Leu Glu Asn Ile Thr Ser Ser Thr Val Ala Phe Lys Ile Lys Thr Thr
            20                  25                  30

Ala Pro Arg Gly Tyr Leu Val Arg Pro Ser Ser Gly Leu Ile Gln Ala
        35                  40                  45

Gly Gln Ser Lys Glu Ile Gln Val Ile Leu Gln Pro Leu Gln Ser Val
    50                  55                  60

Glu Gln Ala Ser Pro Ser His Arg Phe Leu Ile Gln Thr Thr Ala Cys
65                  70                  75                  80

Asp Ser Ser Val Glu Pro Lys Val Ala Glu Asn Lys Ser Ala Ala Asp
                85                  90                  95

Ala Asn Lys Gln Arg Glu Leu Ala Glu Lys Lys Ala Gln Leu Ala Lys
            100                 105                 110

Ala Val Lys Asn Pro Ala Pro Ile Ser Asn Gln Ala Gln Gln Lys Pro
        115                 120                 125

Glu Glu Pro Lys Lys Ser Glu Pro Ala Pro Asn Asn Pro Pro Ala Ala
    130                 135                 140

Asp Ala Pro Ala Ala Gln Ala Pro Ala Ala Pro Ala Glu Pro Ala Pro
145                 150                 155                 160

Gln Asp Lys Pro Ala Asp Ala Pro Ala Ala Glu Ala Pro Ala Ala Glu
                165                 170                 175

Pro Ala Ala Gln Gln Asp Lys Pro Ala Asp Ala
            180                 185
```

NEUTRALIZATION-SENSITIVE EPITOPES OF *CRYPTOSPORIDIUM PARVUM*

RELATED APPLICATIONS

This application is a divisional application of U.S. application Ser. No. 08/916,246, filed Aug. 22, 1997, now U.S. Pat. No. 6,323,020, issued Nov. 27, 2001, which claims priority to U.S. provisional application No. 60/023,440, filed Aug. 23, 1996. The disclosures of these applications are incorporated herein by reference in their entireties.

This invention was made with Government support under National Institutes of Health Grants AI25731, AI30223, and DK34987, and USDA NRICGP grants 94-37204-0496 and 95-01771. The Government has certain rights to this invention.

FIELD OF THE INVENTION

We have cloned and characterized gene fragments encoding epitopes to which sporozoite-neutralizing antibodies are directed. Recombinant proteins and synthetic peptides containing these epitopes are useful for the ability to induce an antigenic response or protection following immunization.

BACKGROUND OF THE INVENTION

Cryptosporidiosis, caused by the protozoal agent *Cryptosporidium parvum*, has emerged as an important enteric disease of humans and animals. *C. parvum* was originally described in 1912, but not recognized as a human pathogen until 1976 [Tyzzer, E. E., *Arch. Protistenkd.*, 26, 394–412 (1912); Meisel, J. L. et al., *Gastroenterol.*, 70, 1156–1160 (1976); Nime, F. A. et al., *Gastroenterol.*, 70, 592–598 (1976)]. The subsequent emergence of AIDS revealed the devastating impact of opportunistic infectious agents, including *C. parvum*, in immunocompromised hosts.

*C. parvum* infects intestinal epithelial cells and induces diarrhea, the duration and severity of which are determined by the immunological competency of the host [Current et al., *N Engl. J. Med.* 308, 1252–1257 (1983); Fayer and Ungar, *Microbiol. Rev.* 50, 458–483 (1986); O'Donoghue, *Int. J. Parasit.* 25, 139–195 (1995)]. Immunocompetent persons become infected following ingestion of a few hundred *C. parvum* oocysts [DuPont, H. L. et al., *N. Engl. J. Med.*, 332, 855–859 (1995)]. Diarrhea lasts 1 to 14 days and ceases with the clearance of infection, a process dependent on CD4[+] T lymphocytes [Ungar, B. L. P. et al., *J. Immunol.*, 147, 1014–1022 (1991); Aguirre, S. A. et al., *Infect. Immun.*, 62, 697–699 (1994); Perryman, L. E. et al., *Infect. Immun.*, 62, 1474–1477 (1994)]. Immunocompetent hosts that recover from infection are generally resistant to reinfection. In contrast, immunodeficient hosts lacking sufficient CD4[+] T lymphocytes develop persistent infections accompanied by severe, life-threatening diarrhea [See, e.g., Petersen, C., *Clin., Infect. Dis.*, 15, 903–909 (1992); Flanigan, T. et al., *Ann. Int. Med.*, 116, 840–842 (1992)]. The management of these patients is complicated by absence of efficacious drugs to control parasite replication [O'Donoghue, supra]. Consequently, investigators have evaluated oral administration of sporozoite- and merozoite-neutralizing antibodies to resolve *C. parvum* infection in hosts lacking sufficient CD4[+] T lymphocytes [Watzl, B. et al., *Am. J. Trop. Med. Hyg.*, 48, 519–523 (1993); Fayer, R. et al., *J. Parasitol.*, 75, 151–153 (1989); Fayer, R. et al., *J. Parasitol.*, 75, 393–397 (1989); Fayer, R. et al., *Infect. Immun.*, 58, 2962–2965 (1990); Doyle, P. S. et al., *Infect. Immun.*, 61, 4079–4084 (1993); Riggs, M. W. et al., *Infect. Immun.*, 62, 1927–1939 (1994); Cama, V. A. and Sterling, C. R., *J. Protozool.*, 38, 42S–43S (1991); Arrowood, M. J. et al., *Infect. Immun.*, 57, 2283–2288 (1989); Bjorneby, J. M. et al., *Infect. Immun.*, 59, 1172–1176 (1991); Perryman, L. E. et al., *Infect. Immun.*, 58, 257–259 (1990); Perryman, L. E., et al., *Infect. Immun.*, 61, 4906–4908 (1993); Tilley, M. et al., *Infect. Immun.*, 59, 1002–1007 (1991).

The demonstrated importance of the immune response in prevention and recovery from *C. parvum* infection has stimulated investigators to define protective immune mechanisms and the characteristics of antigens which induce protective responses. Monoclonal antibodies C6B6, 17.41, 18.44, and 5C3 have been shown to diminish infection by *C. parvum* in neonatal mice. C6B6 reacts with p23; mAb 17.41 reacts with carbohydrate moieties on glycoproteins of 28 to 98 kDa; mAb 18.44 binds to a glycolipid conjugate termed CPS 500; and mAb 5C3 defines glycoproteins of 15 and 60 kDa [Arrowood, M. J. et al., *Infect. Immun.*, 57, 2283–2288 (1989); Tilley, M. et al., *Infect. Immun.*, 59, 1002–1007 (1991); Arrowood, M. J. et al., *J. Parasitol.*, 77, 315–317 (1991); Riggs, M. W. et al., *J. Immunology*, 143, 1340–1345 (1989)]. Other partially protective mAb react with sporozoite proteins and glycoproteins ranging in molecular mass from 25 to >900 kDa (unpublished observations).

SUMMARY OF THE INVENTION

A first aspect of the present invention is an isolated DNA molecule comprising a nucleotide sequence encoding *Cryptosporidium parvum* p23 protein or an antigenic fragment thereof.

A further aspect of the present invention is an isolated DNA molecule encoding a peptide comprising amino acid sequence Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO:4).

A further aspect of the present invention is a method of inducing an antigenic response to *Cryptosporidium parvum*, by administering an antigenic protein or peptide according to the present invention, in an amount sufficient to induce an antigenic response.

A further aspect of the present invention is an antigenic peptide comprising the amino acid sequence: Gln-Asp-Lys-Pro-Ala-Asp (SEQ ID NO:9).

A further aspect of the present invention is a method of inducing an antigenic response to *Cryptosporidium parvum*, by administering to a subject an antigenic peptide comprising the amino acid sequence: Gln-Asp-Lys-Pro-Ala-Asp (SEQ ID NO:9), in an amount sufficient to induce an antigenic response in said subject.

A further aspect of the present invention is a monoclonal antibody that binds to the synthetic peptide Gln-Asp-Lys-Pro-Ala-Asp (SEQ ID NO:9).

A further aspect of the present invention is a method of providing passive immunity to *Cryptosporidium parvum* to a subject, by administration of a monoclonal antibody that binds to the synthetic peptide Gln-Asp-Lys-Pro-Ala-Asp (SEQ ID NO:9).

A further aspect of the present invention is a method of providing passive immunity to *Cryptosporidium parvum* to a subject, by administration of polyclonal antibodies that specifically bind to a peptide comprising the amino acid sequence: Gln-Asp-Lys-Pro-Ala-Asp (SEQ ID NO:9), in an amount sufficient to produce passive immunity in the subject.

Nucleotide sequence data reported in this work are available from the GenBank™ data base with the accession number U34390.

BRIEF DESCRIPTION OF THE DRAWINGS

FIG. 3B—Consensus DNA sequence. The DNA sequence shown is derived from clones depicted in FIG. 2. Predicted amino acid sequence encoded by the longest open reading frame is shown below as single letters and begins with a methionine. A vertical arrow at nucleotide 287 demarcates the beginning of a region rich in PAX (Pro Ala Xaa) and PAAX (Pro Ala Ala Xaa) (SEQ ID NO:10) amino acid motifs. The amino acid sequence encoded by clone C5, which includes the sporozoite neutralization sensitive epitopes, is underlined. A potential N-linked glycosylation site is shown in bold, beginning with amino acid 15. Nucleotide primer sequences used for PCR amplification of C. parvum DNA and RNA (see FIG. 4) are also underlined.

DETAILED DESCRIPTION OF THE INVENTION

Figure 1:
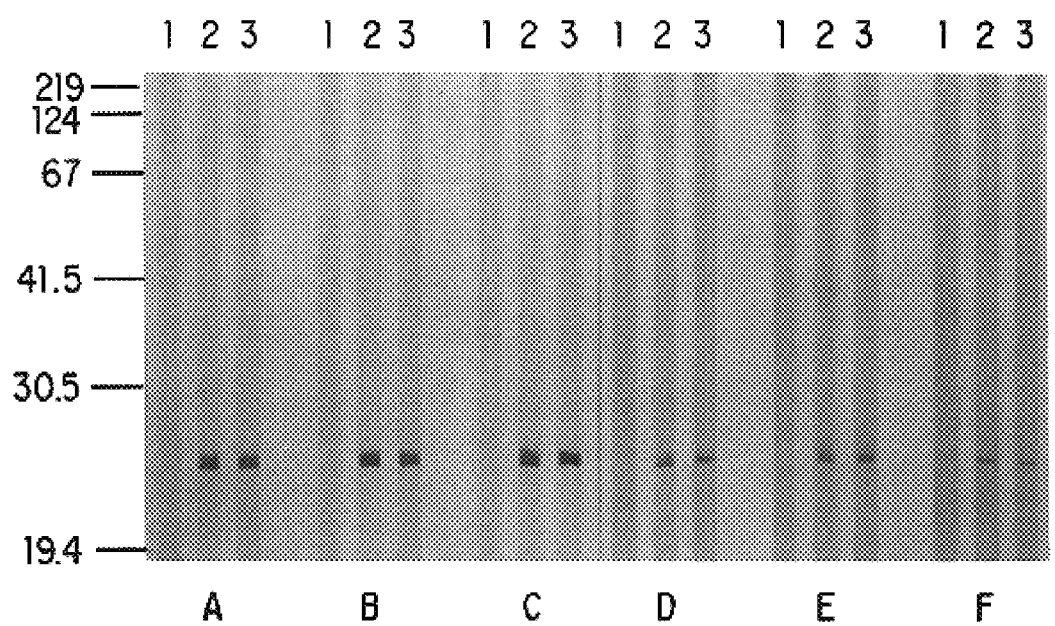
FIG. 1—Western immunoblots of C. parvum isolates. C. parvum sporozoites were obtained from Iowa (A), New York (B), Florida (C), Mexico (D), Brazil (E) and Peru (F). Each isolate was probed with IgG$_1$ isotype control mAb (lane 1), mAb C6B6 (lane 2), and mAb 7D10 (lane 3). MW standards (in thousands) are indicated on the left.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., Patent In User Manual, 99–102 (November 1990) (U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend that the disclosure of this and all other patent references cited herein be incorporated herein by reference). Single letter amino acid code is provided for convenience.

DNA molecules useful for carrying out the present invention include those coding for *Cryptosporidium parvum* p23 protein, and particularly for proteins homologous to, and having essentially the same biological properties as, the protein given herein SEQ ID NO:2. This definition is intended to encompass natural allelic variations therein. Isolated DNA or cloned genes of the present invention can be of any strain of C. parvum. Thus, DNAs which hybridize to DNA disclosed herein as SEQ ID NO:1 and which code on expression for a protein of the present invention (e.g., a protein according to SEQ ID NO:2) are also an aspect of this invention.

Conditions which will permit other DNAs which code on expression for a protein of the present invention to hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively) to DNA of SEQ ID NO:1 disclosed herein in a standard hybridization assay. See, e.g., J. Sambrook et al., Molecular Cloning, A, Laboratory Manual (2d Ed. 1989)(Cold Spring Harbor Laboratory)). In general, sequences which code for proteins of the present invention and which hybridize to the DNA of SEQ ID NO:1 disclosed herein will be at least 75% homologous, 85% homologous, and even 95% homologous or more with SEQ ID NO:1.

DNAs which code for proteins of the present invention, or DNAs which hybridize to that of SEQ ID NO:1, but which differ in codon sequence from SEQ ID NO:1 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

The production of cloned genes, recombinant DNA, vectors, transformed host cells, proteins and protein fragments by genetic engineering is well known. See. e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding proteins or peptides as given herein and/or to express DNA which encodes proteins or peptides as given herein. An expression vector is a replicable DNA construct in which a DNA sequence encoding a protein or peptide as given herein is operably linked to suitable control sequences capable of effecting the expression of the DNA sequence in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Typical vectors include, but are not limited to, plasmids, viruses, phage, and integratable DNA fragments (i.e., fragments integratable into the host genome by recombination).

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a DNA sequence as disclosed herein constructed using recombinant DNA techniques. Transformed host cells ordinarily express the receptor, but host cells transformed for purposes of cloning or amplifying the receptor DNA do not need to express the receptor.

Suitable host cells include prokaryote, yeast or higher eukaryotic cells such as mammalian cells and insect cells. Cells derived from multicellular organisms are a particularly suitable host for recombinant protein or peptide synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, and Chinese hamster ovary (CHO) cell lines. Expression vectors for such cells ordinarily include (if necessary) an origin of replication, a promoter located upstream from the DNA encoding the protein or peptide to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See. e.g., U.S. Pat. No. 4,599,308.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the receptor DNA. Examples of suitable selectable markers are dihydrofolate reductase (DHFR) or thymidine kinase. This method is further described in U.S. Pat. No. 4,399,216.

Host cells such as insect cells (e.g., cultured *Spodoptera frugiperda* cells) and expression vectors such as the baculovirus expression vector may be employed in carrying out the present invention, as described in U.S. Pat. Nos. 4,745,051 and 4,879,236 to Smith et al.

Prokaryote host cells include gram negative or gram positive organisms, for example *Escherichia coli* (*E. coli*) or Bacilli.

Eukaryotic microbes such as yeast cultures may also be transformed with vectors carrying the isolated DNAs disclosed herein. See. e.g., U.S. Pat. No. 4,745,057. *Saccharomyces cerevisiae* is the most commonly used among lower eukaryotic host microorganisms, although a number of other strains are commonly available.

B. Peptides

One group of exemplary antigenic fragments of the present invention, useful in the methods of this invention, are antigenic peptides having an amino acid sequence selected from the group consisting of:

Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO:4);

Gln Asp Lys Pro Ala Asp (SEQ ID NO:9); and longer peptides that include the sequence of an antigenic peptide as described above. Longer peptides provide the antigenic sequence in an exposed position on the molecule, and not buried in the interior of the molecule where it would be unavailable for a binding event. Longer peptides which add not more than four or six additional amino acids to either the N terminal or C terminal of the antigen are preferred because sequences of such length are generally insufficient to provide an additional epitope on the longer peptide which might be detrimental to the activity of the antigen. Longer peptides encompass the sequence of an antigenic peptide as described above within a fragment of the protein, the fragment representing a single continuous segment of the protein amino acid sequence.

C. Methods of Inducing Antigenic and Immunogenic Responses

As noted above, the present invention provides a method comprising administering an animal subject an antigen as described above (e.g., a protein or peptide as described above) in an amount effective to produce an antigenic response (i.e., cause the production of antibodies that specifically bind to the immunogen) or an immunogenic response (i.e., cause the mounting of an immune response upon subsequent introduction of the antigen into the animal) in the subject. As used herein, an immunogenic response includes an antigenic response. The antigen may be administered directly or indirectly by way of a nucleic acid intermediate, as discussed below.

Any animal may be treated by the method of the present invention, including both birds and mammals. Exemplary mammals include rabbits, dogs, cats, cows, pigs, sheep, horses, non-human primates and humans. Mammalian subjects are preferred. The antigen may be administered to the subject by any suitable means. Exemplary are by intramuscular injection, by subcutaneous injection, by intravenous injection, by intraperitoneal injection, by oral administration, and by nasal spray.

The antigen may be administered to an animal subject to produce polyclonal antibodies that bind specifically to a protein described herein, and the antibodies then collected in accordance with known techniques from blood, serum, colostrum, egg yolks, etc. The antibodies so collected may be used to impart passive immunity to C. parvum in an animal subject in need thereof, or in diagnostic tests for C. parvum.

The amount of antigen administered will depend upon factors such as route of administration, species being immunized, health status of subject being immunized, and the use of booster administrations, as would be apparent to one skilled in the art. In general, a dosage of from about 0.01, 0.1, 0.3, 0.5 or 1.0 $\mu$g per pound (from about 0.022, 0.22, 0.66, 1.1, or 2.2 $\mu$g per kilogram), to about 5.0, 10.0, 50.0 or 100 $\mu$g per pound (to about 11.0, 22.0, 110.0, or 220.0 $\mu$g per kilogram) subject body weight may be used, more particularly from about 0.1 $\mu$g per pound to about 10 $\mu$g per pound (from about 0.22 $\mu$g per kilogram to about 22 $\mu$g per kilogram), and more particularly from about 0.1 $\mu$g per pound to about 1.0 $\mu$g per pound (from about 0.22 $\mu$g per kilogram to about 2.2 $\mu$g per kilogram).

The method of the present invention contemplating both human and veterinary treatments, the antigens of the present invention may be prepared as both human and veterinary formulations. Formulations of the present invention comprise the appropriate antigen in a pharmaceutically acceptable carrier. The antigen is included in the carrier in an amount effective to induce an antigenic or immunogenic response in the subject being treated. Vaccine formulations may comprise combinations of appropriate antigens. Pharmaceutically acceptable carriers are preferably liquid, particularly aqueous, carriers, such as sodium phosphate buffered saline. The formulation may be stored in a sterile glass container sealed with a rubber stopper through which liquids may be injected and formulations withdrawn by syringe.

Formulations of the present invention may optionally contain one or more adjuvants. Any suitable adjuvant can be used, exemplary being aluminum hydroxide, aluminum phosphate, plant and animal oils, and the like, with the amount of adjuvant depending on the nature of the particular adjuvant employed. In addition, the formulations may also contain one or more stabilizers, exemplary being carbohydrates such as sorbitol, mannitol, starch, sucrose, dextrin, and glucose, proteins such as albumin or casein, and buffers such as alkaline metal phosphate and the like, which may be linked to the antigen in accordance with known techniques.

DNA Administration. Antigens may be administered to the subject by administering a nucleic acid that expresses the antigen in the subject in an antigenically or immunogenically effective amount. The antigen may be administered to the subject by administering a gene transfer vector such as a recombinant virus (including those modified from DNA viruses and RNA viruses) that infect the cells of the subject and express the nucleic acid therein, or by direct DNA administration.

Direct DNA administration may be carried out by injecting an isolated polynucleotide that includes a DNA sequence encoding the antigen linked to a promoter sequence which expresses the DNA antigen-encoding sequence in the subject, in an amount sufficient that uptake of the construct occurs, and sufficient expression results to induce an antigenic or immunogenic response to the encoded antigen. Such techniques are described in U.S. Pat. No. 5,589,466 to P. Felgner et al. (assigned to Vical Inc. and the Wisconsin Alumni Research Foundation)(the disclosure of all U.S. Patents recited herein is incorporated herein by reference).

Direct DNA administration may also be carried out as described by S. Johnston et al. in European Patent Application No. 91901057.9-2105 to Duke University, filed Nov. 13, 1990. In this technique, microparticles that carry a DNA sequence encoding the antigen linked to a promoter sequence that expresses the antigen in the subject are used to bombard skin tissue cells so that the particles enter the skin tissue cells, in an amount sufficient to induce an antigenic or immunogenic response to the encoded antigen.

Antibodies produced in subjects by the methods described above can be collected and purified by known techniques and administered to a subject to impart passive immunity to Cryptosporidium parvum to that subject. Antibodies can also be collected and used in diagnostic assays to detect C. parvum.

The present invention is explained below in the Examples set forth below.

EXAMPLE 1

Materials and Methods

A cDNA library was prepared from sporozoite mRNA and screened with mAb shown to bind peptide epitopes of C. parvum antigens and to reduce infection in a suckling mouse challenge model. An open reading frame (ORF) encoding two distinct neutralization-sensitive epitopes found within p23, a surface glycoprotein of C. parvum sporozoites, was defined. One of the epitopes is linear and occurs twice in a 27 amino acid portion of the peptide encoded by the 3' end of the cloned gene fragment. The second epitope is within the same 27 amino acid region, but may be dependent on conformation of the peptide.

Cryptosporidium Parvum Organisms

The Iowa isolate of C. parvum was originally obtained from H. Moon, Ames, I A [Heine, J., et al., J. Inf. Dis., 150, 768–775 (1984)]. Additional C. parvum oocysts were obtained from humans or calves from Florida, New York, Mexico, Brazil, and Peru [Uhl, E. W. et al., Infect. Immun., 60, 1703–1706. (1992)]. Oocysts were maintained by passage through neonatal calves and prepared as previously described [Riggs, M. W. and Perryman, L. E., Infect. Immun., 55, 2081–2087 (1987)]. To obtain sporozoites, oocysts were treated with 1.75% Na hypochlorite for 8 minutes at 4° C., washed thoroughly, resuspended in HBSS, and incubated for 1.5 hr at 37° C. in a shaking water bath. The resulting mixture of intact oocysts, oocyst shells, and free-sporozoites was applied to DE-52 DEAE cellulose columns. Sporozoites were eluted with equilibration buffer and solubilized in the presence of protease inhibitors as previously described [Riggs, supra].

Preparation of mAb

The preparation and characterization of mAb C6B6 was previously described [Arrowood, M. J. et al., Infect. Immun., 57, 2283–2288 (1989); Arrowood, M. J. et al., J. Parasitol., 77, 315–317 (1991)]. This IgG$_1$ antibody binds to a sporozoite surface antigen with M$_r$ of 23 kDa, and partially protects mice against infection by C. parvum. The p23 antigen of *C. parvum* was purified by affinity chromatography employing mAb C6B6 as binding ligand [Riggs, M. W. et al., Molecular targets for passive immunotherapy of cryptosporidiosis. 47*th Ann. Meet. Soc. Protozool.* and 3*rd Workshop on Pneumocystis, Toxoplasma, Cryptosporidum and Microsporidia*. June 24–29. Cleveland, Ohio, Abst. C46, 76 (1994)]. Adult female BALB/c mice (Harlan Sprague Dawley, Indianapolis, Ind.) were immunized with 2 ug isolated p23 antigen incorporated in monophosphoryl lipid A trehalose dimycolate adjuvant (R-700, Ribi, Hamilton, Mont.) and administered i.p. and s.c. A second injection of 1 ug p23 in adjuvant was given 7 weeks later by the same routes. Four weeks later, a third injection of 1 ug p23 in adjuvant was given s.c. A final i.v. injection of 1.5 ug p23 in PBS was given 5 weeks later. Three days following i.v. injection, the spleen was removed and a single cell suspension prepared for fusion with SP2/0 myeloma cells. Hybridomas were screened, cloned, and cryopreserved as previously described [Riggs, M. W. et al., *J. Immunology*, 143, 1340–1345 (1989)]. One of the resulting mAb, designated 7D10, was selected for further characterization. The ability of mAb 7D10 and C6B6 to bind sporozoite antigen following oxidation with 7 mM Na periodate [Woodward, M. P. et al., *J. Immunol. Methods*, 78, 143–153 (1985)], or treatment with 2 ug proteinase K for 1 hr at 56° C., was determined by immunoblot assay.

Mouse Infection Assay

Neonatal BALB/c mice develop intestinal infections following oral administration of $10^4$ peracetic acid-disinfected *C. parvum* oocysts [Riggs, M. W. and Perryman, L. E., *Infect. Immun.*, 55, 2081–2087 (1987)]. Ability of mAb C6B6 and 7D10 to diminish infection was tested by orally administering 100 ul of ascites containing the mAb at the time of, as well as 2 and every 12 hours following oral challenge with $10^4$ oocysts. Control mice were administered $IgG_1$ mAb of irrelevant specificity. Mice were terminated 92 to 94 hours following oocyst administration. Intestinal tracts were removed and scored histologically for the presence and number of *C. parvum* organisms in epithelial cells of the ileum, cecum, and colon [Riggs, M. W. and Perryman, L. E., *Infect. Immun.*, 55, 2081–2087 (1987)]. Scores of 0 to 3 were assigned for each of the three sites, with 0 indicating no organisms; 1, <33% of cells parasitized; 2, 33 to 66% of cells parasitized; and 3, >than 66% of cells parasitized. Scores from the three sites were summed to obtain an infection score for each mouse. Score differences between groups of mice were analyzed by Student's t test.

Preparation and Analysis of Genomic DNA and cDNA Libraries of *C. parvum*

Genomic DNA was extracted from $1 \times 10^9$ oocysts which had been previously frozen [−80° C.] in PBS. The oocysts were diluted with 5 volumes of lysis buffer containing 100 mM NaCl, 200 mM EDTA, 50 mM Tris (pH 7.5), 0.5% SDS and heated at 65° C. for 15 minutes. The solution was next incubated at 42° C. with proteinase K (100 ug/ml) for 24 hours. Sodium chloride was added to a concentration of 1 M and the mixture extracted with phenol and chloroform. The DNA was ethanol precipitated, treated with RNase A (15 ug/ml) and RNase Ti (15 units/ml) at 42° C. for 30 minutes. Proteinase K (100 ug/ml) was added and the mixture further incubated at 42° C. for 1 hour. Sodium chloride was added to a concentration of 100 mM and the mixture extracted with phenol and chloroform. The DNA was ethanol precipitated and then suspended in 10 mM Tris, 0.1 mM EDTA (pH 8.0). This DNA preparation contained significant non-nucleic acid precipitate. Because of limited parasite material, isolated DNA was further purified by electrophoresis in a 0.7% agarose (NuSieve GTG low-melting agarose) gel, followed by isolation of the ethidium bromide-stained DNA.

Total RNA was isolated from excysted sporozoites by acid guanidinium extraction [Chomczynski, P. and Sacchi, N., *Analyt. Biochem.*, 162, 156–159 (1987)]. mRNA for cDNA production was isolated by oligo-dT cellulose chromatography. cDNA was prepared using a Zap-cDNA synthesis kit (Stratagene, La Jolla, Calif.). Double stranded cDNA was synthesized with Eco RI (5' end) and Xho I (3' end) sticky ends and then ligated into UniZap-XR. Ligated DNA was packaged using Gigapak II gold packaging and amplified in *Escherichia coli* strain PLK-F'. The preamplified library produced an estimated $1.7 \times 10^6$ phage.

The cDNA expression library was screened using methods described elsewhere [Chomczynski, P. and Sacchi, N., *Analyt. Biochem.*, 162, 156–159 (1987)]. Briefly, antisera from a cow hyperimmunized with *C. parvum* sporozoites [Riggs, M. W. and Perryman, L. E., *Infect. Immun.*, 55, 2081–2087 (1987)] was used as primary antibody for screening. $^{125}$I-conjugated protein G was used to detect primary antibody binding to phage protein adsorbed onto nitrocellulose. Purified clones were then rescreened with mAb C6B6 and 7D10. Vector and insert from mAb-positive clones were converted from phage to plasmid constructs via in vivo excision (Stratagene, La Jolla, Calif.). DNA sequencing, performed with sequentially-derived sequencing primers, indicated that initial clones lacked a complete coding sequence.

To identify the entire gene sequence that encodes the protein containing the neutralization sensitive epitopes, a DNA fragment from clone C7 and a polymerase chain reaction-amplified DNA product from clone C11 were used to rescreen the library. A DNA fragment from the C7 insert was produced by digesting cloned plasmid DNA with StyI and Bam HI, at sites which were within the cDNA sequence and polycloning site, respectively. A 5' 352 bp fragment of C7 was isolated from agarose gel and used in DNA hybridization reactions with phage plaques as described [Jasmer, D. P. et al., *J. Parasitol.*, 76, 834–841 (1990)]. This allowed identification of clone C11. A PCR-amplified probe fragment was made by using primers generated from the C11 clone sequence (FIGS. 2 and 3) to amplify C11 plasmid DNA (1 ug of plasmid DNA in each reaction). This 208 bp 5' gene product was then used to screen the cDNA library. Both restriction enzyme and PCR generated DNA fragments were labeled with dATP-$\alpha$-$^{32}$P using a random primer kit (Boerhinger Mannheim, Indianapolis, Ind.).

Reverse transcriptase-PCR (RT-PCR) amplification of total RNA (1 ug in each reaction) was done essentially as described [Jasmer, D. P., *J. Cell Biol.*, 121, 785–793. (1993)], and this procedure, excluding the RT step, was also used to amplify genomic DNA (100 ng in each reaction). PCR products amplified from total RNA and genomic DNA were hybridized to PCR-amplified probes from plasmid-C11 by Southern blot procedures as described [Jasmer, D. P., *J. Cell Biol.*, 121, 785–793. (1993)].

EXAMPLE 2

Definition of the ORF Sequence Encoding the Epitopes Defined by mAb C6B6 and 7D10

Since clones C1, C2, C5, C6, C7, and C8 shared common 3' sequences, the shortest sequence (C5),was used for epitope mapping studies. Nested sets of hexamer peptides spanning the C terminal 27 amino acid sequence deduced from C5 were synthesized using commercial reagents and instructions (SPOTs Test, Cambridge Research Biochemicals, Cheshire, England). The ability of mAb C6B6 and 7D10 to bind linear hexamer epitopes was determined by manufacturer's instructions. In addition, the entire 27 amino acid peptide was synthesized (Bioanalytical Services Laboratory, Washington State University, Pullman, Wash.) and tested in a dot blot assay for ability to bind mAb C6B6 and 7D10.

Western Blot Assays

C. parvum oocysts were excysted and liberated sporozoites solubilized in lysis buffer (50 mM Tris, 5 mM EDTA, 5 mM iodoacetamide, TLCK, 1 mM PMSF, 1% octyl glucoside, and 1% [v/v] NP-40) as described [Riggs, M. W. et al., J. Immunology, 143, 1340–1345 (1989)]. Antigens were resolved by SDS-PAGE (10–20% gradient, reducing conditions), transferred to nitrocellulose, probed with mAb at 25 ug/ml, and detected colorimetrically with alkaline phosphatase-conjugated, affinity purified rabbit anti-mouse $IgG_1$ secondary antibody (Zymed, South San Francisco, Calif.). Recombinant C. parvum antigen rC5, and control recombinant protein (rCo) were prepared by expanding host bacteria and incubating in 10 mM IPTG for 4 hr. Bacteria were disrupted by incubation in lysis buffer containing 1 mg/ml lysozyme, followed by sonication for 15 seconds on ice. Clarified lysates were resolved by SDS-PAGE on 10% gels, transferred to nitrocellulose membranes, probed with mAb, and visualized by chemiluminescence following incubation with horse radish peroxidase-conjugated goat anti-mouse IgG secondary antibody (Cappel, Organon Teknika, Durham, N.C.) and ECL reagent (Amersham Life Science, Arlington Heights, Ill.).

Dot Blot Assay

Synthetic peptides (1 ug C. parvum peptide:
QDKPADAPAAEAPAAEPAAQQDKPADA (Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO:4)(row A);
or 1 ug control peptide:
KESQAYYDGRRSSAVL (Lys Glu Ser Gln Ala Tyr Tyr Asp Gly Arg Arg Ser Ser Ala Val Leu) (row B) (SEQ ID NO:5)
were applied to discrete spots on a nitrocellulose membrane, washed with methanol, and reacted with mAb at 70 ug/ml. Reactions were visualized by chemiluminescence as described above.

Mouse Immunization With Synthetic Peptide

The extended peptide:
CLAPQDKPADAPAAEAPAAEPAAQQDKPADA (Cys Leu Ala Pro Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO:3)
was synthesized, and then linked to maleimide-activated keyhole limpet hemocyanin (KLH-) according to manufacturer's instructions (Pierce, Rockford, Ill.). Adult BALB/c mice were immunized three times at two week intervals with 100 ug KLH-extended peptide incorporated in monophosphoryl lipid A trehalose dimycolate adjuvant (R-700, Ribi, Hamilton, Mont.) and administered s.c. Preimmune and immune serum were tested for ability to bind sporozoite antigens in western immunoblot assay, as described above.

EXAMPLE 3

Results

Characteristics of mAb C6B6 and 7D10

Monoclonal antibodies C6B6 and 7D10 bind to geographically-conserved epitopes of the p23 C. parvum sporozoite surface antigen (FIG. 1). Both mAb retained ability to bind p23 following oxidation of sporozoite antigens with 7 mM Na periodate, but not following treatment of sporozoite antigens with 2 ug proteinase K for 1 hr at 56° C. This suggested that their respective epitopes were peptide rather than carbohydrate. Both mAb significantly diminish infection of neonatal mice when challenged orally with $10^4$ C. parvum oocysts (Table I).

TABLE I

Partial protection of mice against Cryptosporidium parvum oocyst challenge with mAb C6B6 and 7D10, individually and in combination

| Expt. No. | Monoclonal Antibody | # Mice Infected/ # Challenged | Infection Score (Mean ± S.D.) | Significance versus control (p <) |
|---|---|---|---|---|
| I | Control[a] | 9/9 | 6.1 ± 1.4 | — |
|  | C6B6 alone | 9/9 | 3.9 ± 0.8 | 0.0005 |
|  | 7D10 alone | 9/9 | 4.1 ± 0.6[b] | 0.0005 |
|  | C6B6 + 7D10[c] | 9/9 | 3.4 ± 0.5[b] | 0.0001 |
| II | Control[a] | 9/9 | 6.6 ± 0.5 | — |
|  | C6B6 alone | 10/10 | 4.7 ± 0.8 | 0.0001 |
|  | 7D10 alone | 9/9 | 5.4 ± 0.7 | 0.001 |
|  | C6B6 + 7D10[c] | 10/10 | 4.8 ± 1.1 | 0.0005 |

[a]Isotype-matched $IgG_1$ mAb ascites of irrelevant specificity.
[b]These two values are significantly different from each other (p < 0.05).
[c]Equal volumes of each mAb ascites were pooled.

Characteristics of the ORF Encoding the Epitopes Defined by mAbs C6B6 and 7D10

The cDNA library was screened with serum obtained from a cow repeatedly immunized with C. parvum sporozoites and merozoites [Riggs, M. W. and Perryman, L. E., supra; Perryman, L. E. and Bjorneby, J. M. J. Protozool., 38, 98S–100S (1991)]. Immune bovine serum identified multiple recombinant phage which were purified to homogeneity. When analyzed by Western blot using immune bovine serum, the recombinant fusion proteins from clones C1 through C8 ranged from 16 to 31 kDa $M_r$ (data not shown). Furthermore, the recombinant proteins from each of these clones reacted with mAb C6B6 and 7D10.

Figures 2, 3A:
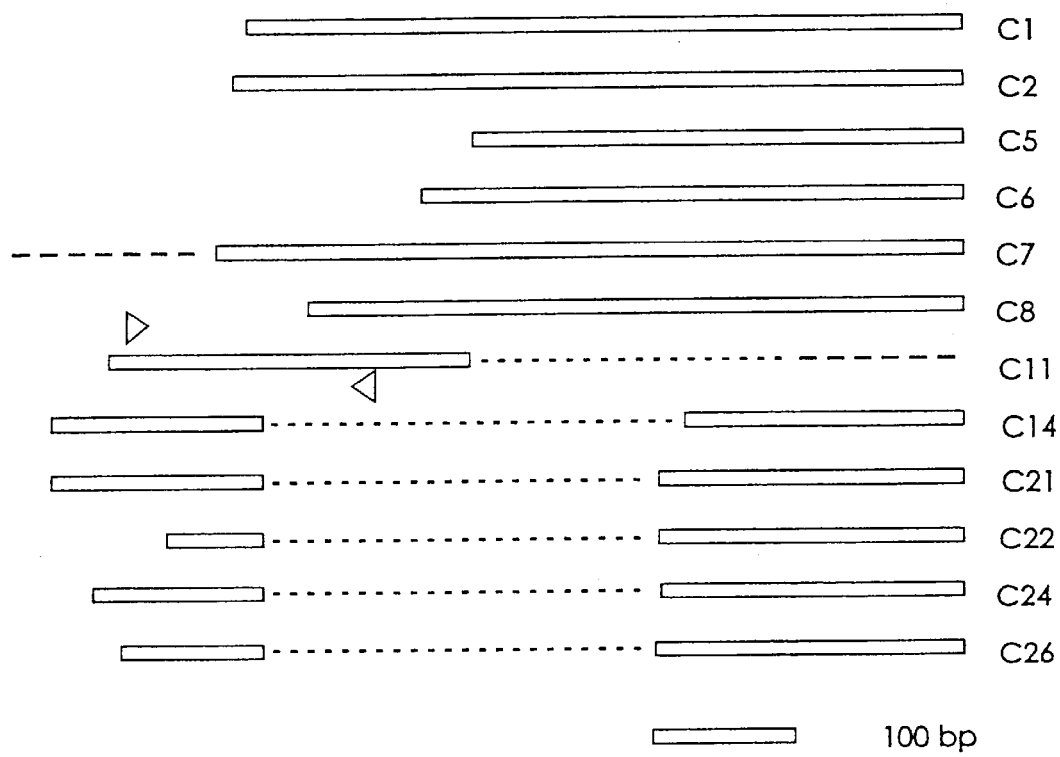
FIG. 2—Relationship of cDNA clones. Clones C1, 2, 5, 6, 7 and 8 were initially identified by expression screening with polyclonal antibody from a cow hyperimmunized with C. parvum sporozoites, and mAb C6B6 and 7D10. C11 was identified by screening with a 5' probe obtained from C7, its 3' Sty I terminus indicated by a vertical hash mark. C14, 21, 22, 24, and 25 were identified by screening with a PCR-generated fragment of C11 (arrow-heads demarcate 5' and 3' PCR primers). Sequence identity among clones is indicated by solid lines, sequence divergence from consensus is indicated by dots and unsequenced regions of clones are indicated by dashes. Unsequenced region of C11 is not drawn to scale.
FIG. 3A—Predicted amino acid sequence encoded by the longest open reading frame. The sequence encoded by clone C5, which includes the sporozoite neutralization sensitive epitopes, is underlined. A potential N-linked glycosylation site, beginning with amino acid 15, is double underlined.
Figure 4:
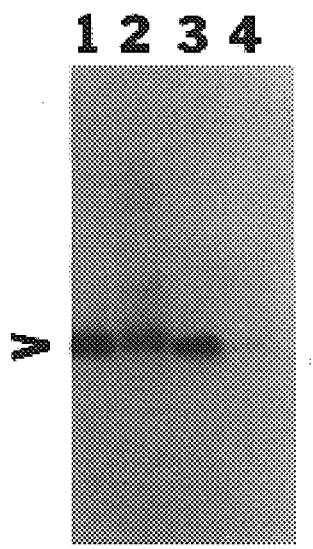
FIG. 4—PCR amplification of C. parvum RNA and DNA using primers from the consensus gene sequence. PCR primers from the 5' untranslated (sense) and 3' untranslated (antisense) sequences were used to authenticate existence of the consensus gene sequence in C. parvum. Genomic DNA (100 ng) (Lane 1), C14 plasmid DNA (1 ng) (Lane 2), or total RNA (1 ug) with (lane 3) or without (Lane 4) reverse transcriptase was amplified by PCR, electrophoresed on a 0.7% agarose gel, Southern blotted and probed with the C11 PCR probe (delineated in FIG. 2). The arrow designates the 486 bp product anticipated from the consensus sequence.

Sequence data from selected cDNAs are diagrammed in FIG. 2. The consensus nucleotide sequence and amino acid translation of a complete ORF encoding the epitopes for mAb C6B6 and 7D10 are shown (FIG. 3). To authenticate the presence of this sequence in C. parvum DNA and total RNA, primers derived from the consensus sequence were used in PCR reactions (FIG. 4). These primers led to amplification of a predicted 486 bp product from genomic DNA, C14 plasmid, and total RNA, which in the latter case was RT-dependent. These results confirm the reliability of the consensus gene sequence and indicate that the coding sequence is not interrupted by introns in genomic DNA. In contrast, primer sets which included C7 5' sequence or C11 3' sequence did not generate PCR products. These observations indicate that the 5' sequence of the C7 clone and the 3' sequence of the C11 clone represent cloning artifacts.

The predicted amino acid sequence of the only extensive open reading frame has a methionine and encodes a protein of 11.3 kDa. The predicted protein lacks apparent signal sequences or hydrophobic sequences consistent with a membrane protein. It does contain one potential N-glycosylation site, as well as potential O-glycosylation sites (FIG. 3). The amino acid sequence is relatively rich in alanine (29%) and proline (17%). A region in the carboxyl terminal-half of the protein is highly enriched for these amino acids and has redundant PAX or PAAX motifs (FIG. 3). Each of the expressor clones identified by mAb C6B6 and 7D10 included this region of the protein, suggesting the location of the corresponding epitopes.

EXAMPLE 4

Budapest Treaty Deposit

Clones C25, C5, and C7, which together contain the entire cDNA sequence of the p23 protein, were deposited in accordance with the provisions of the Budapest Treaty at the American Type Culture Collection (12301 Parklawn Drive, Rockville, Md. 20852 USA) on Aug. 28, 1996 in the following strains, which were assigned the following ATCC designation numbers:

Cryptosporidium parvum C25, pBSK; XL-1 Blue Escherichia coli ATCC No: 98157;

C. parvum C5, pBSK; XL-1 Blue E. coli ATCC No: 98158;

C. parvum C7, pBSK; XL-1 Blue E. coli ATCC No: 98159.

EXAMPLE 5

Identification of Epitopes Defined by mAb C6B6 and 7D10

Figure 5:
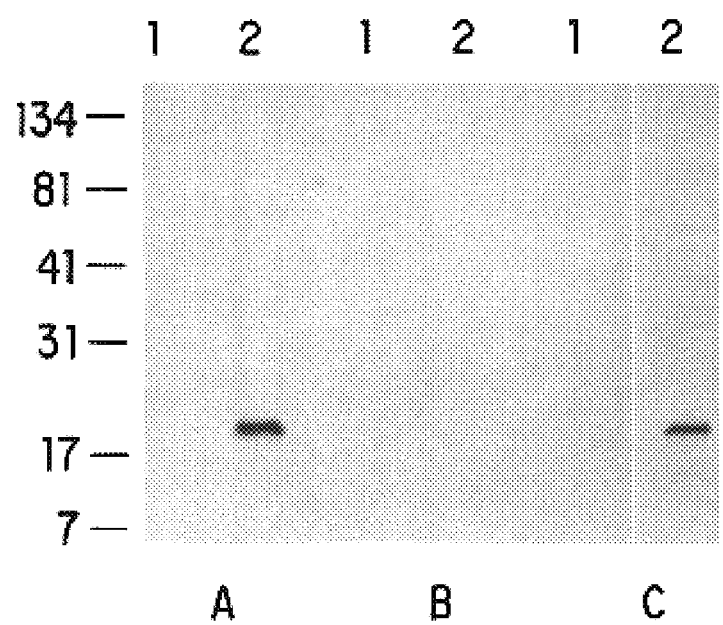
FIG. 5—Western immunoblots of recombinant and control proteins. Recombinant control protein (lane 1) and C. parvum rC5 (SEQ ID NO:11) (lane 2) were probed with mAb 7D10 (A), IgG$_1$ isotype control mAb (B) and mAb C6B6 (C). MW standards (kDa) are indicated on the left.
Figure 6:
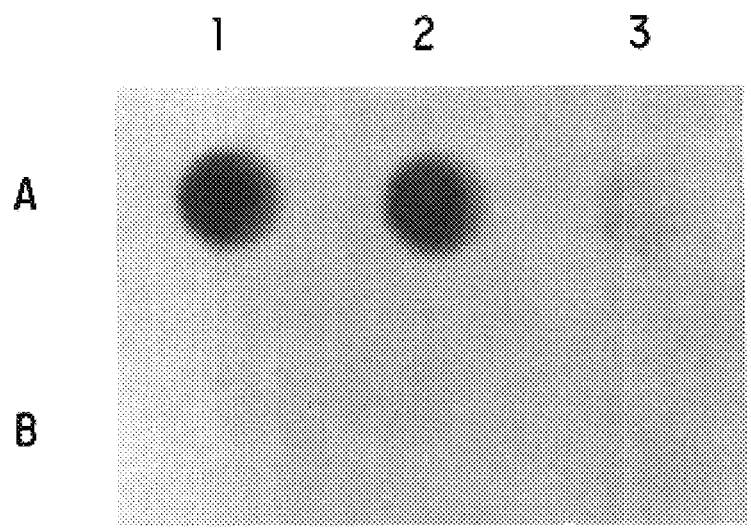
FIG. 6—Dot blots of synthetic peptides. Synthetic C. parvum peptide QDKPADAPAAEAPAAEPAAQQDK-PADA (Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO: 4)(row A) or control peptide KESQAYYDGRRSSAVL (Lys Glu Ser Gln Ala Tyr Tyr Asp Gly Arg Arg Ser Ser Ala Val Leu) (SEQ ID NO:5)(row B) were probed with mAb 7D10 (lane 1), mAb C6B6 (lane 2), or isotype control IgG$_1$ mAb (lane 3).
Figure 7:
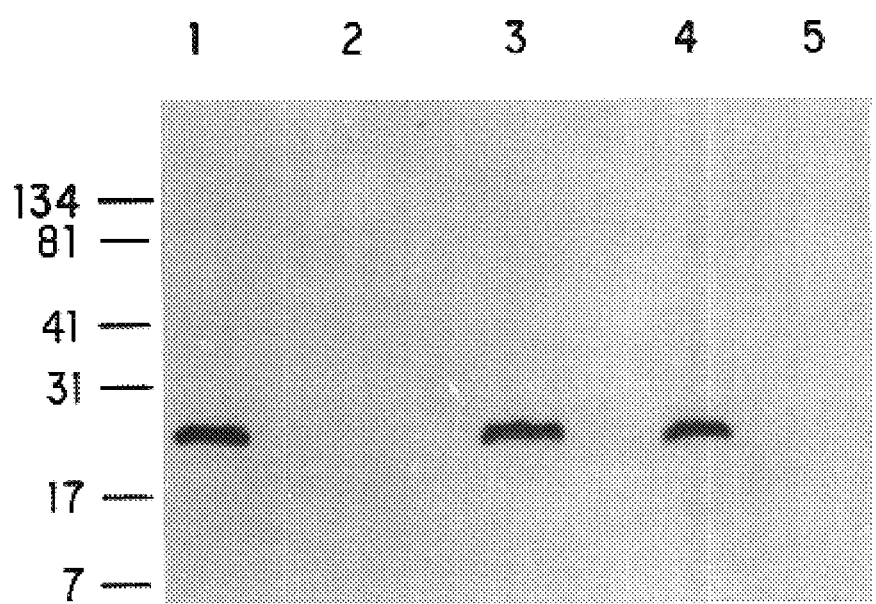
FIG. 7—Western immunoblots of C. parvum. Sporozoite antigens were probed with mAb 7D10 (lane 1); IgG$_1$ control mAb (lane 2); mAb C6B6 (lane 3); serum from mice immunized with CLAPQDKPAD APAAE-APAAEPAAQQDKPADA (Cys Leu Ala Pro Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO:3) linked to keyhole lympet hemocyanin (lane 4); and preimmune mouse serum (lane 5). MW standards (kDa) are indicated on the left.

Since both mAb bound a peptide encoded by the 3' end of clones C1–C8, the amino acid translation of the shortest clone, C5, was utilized to define the binding epitopes. MAb C6B6 and 7D10 bound to rC5, and to the 27 amino acid synthetic peptide predicted from the 3' terminal nucleotide sequence of C5 (SEQ ID NO:11) (FIGS. 5 and 6). Antibody 7D10 bound the hexamer sequence QDKPAD (SEQ ID NO:9) which occurs twice in the 27 amino acid peptide (SEQ ID NO:4) encoded by the 3' end of the ORF. The nucleotide sequence encoding QDKPAD does not appear elsewhere in the ORF. Antibody C6B6 did not bind to any of the hexamer peptides, nor did it bind to any of the three overlapping 12 mer peptides QDKPADAPAAEA (Gln Asp Lys Pro Ala Asp Ala Pro Ala Ala Glu Ala)(SEQ ID NO:8), AAEAPAAEPAAQ (Ala Ala Glu Ala Pro Ala Ala Glu Pro Ala Ala Gln) (SEQ ID NO:7), and EPAAQQDKPADA (Glu Pro Ala Ala Gln Gln Asp Lys Pro Ala Asp Ala) (SEQ ID NO:6)(data not shown). C6B6 does bind to the entire 27 amino acid peptide (FIG. 6). These observations suggest the epitope for mAb C6B6 is conformation-dependent rather than linear. Mice immunized with keyhole limpet hemocyanin-CLAPQDKPADAPAAEAPAA EPAAQQDK-PADA (Cys Leu Ala Pro Gln Asp Lys Pro Ala Asp Ala Pro Ala Ala Glu Ala Pro Ala Ala Glu Pro Ala Ala Gln Gln Asp Lys Pro Ala Asp Ala) (SEQ ID NO:3) produced antibodies that reacted with a single sporozoite antigen of approximately 23 kDa (FIG. 7).

EXAMPLE 6

Discussion of Results

The mAb (C6B6 and 7D10) described herein share important characteristics. Both bind to amino acid epitopes of a surface-exposed 23 kDa protein of C. parvum sporozoites. This protein is a common target for antibody response in animals and humans exposed to C. parvum [See, e.g., Whitmire, W. M. and Harp, J. A. Infect. Immun., 59, 990–995 (1991); Reperant, J.-M., et al., Vet. Parasitol., 55, 1–13 (1994); Mead, J. R. et al., J. Parasitol., 74, 135–143 (1988); Tilley, M. et al., FEMS Microbiol. Lett., 113, 235–240 (1993)]. Since p23 may be involved in sporozoite motility, it is a useful target for immunological intervention. The epitopes recognized by mAb C6B6 and 7D10 are both conserved among geographical isolates of C. parvum, suggesting they are not subject to antigenic variation. Previously, we showed that other neutralizing mAb bound to carbohydrate or glycolipid epitopes from these same disperse isolates of C. parvum sporozoites [Uhl, E. W. et al., Infect. Immun., 60, 1703–1706. (1992)]. No evidence yet exists for the occurrence of antigenic variation in C. parvum, as tested with neutralizing antibodies. If antigenic variation of functionally-important, neutralization-sensitive epitopes of C. parvum does not occur, it will simplify development of immunization strategies to protect against cryptosporidiosis. Finally, both mAb diminished infection when tested in a neonatal mouse oral oocyst challenge model. This is a rigorous test of neutralizing capacity in that mAb must bind to sporozoites in the short time between excystation of oocysts in the intestinal lumen and successful attachment to, and penetration of, intestinal epithelial cells. Ability of mAb to inhibit infection is dependent on time of in vitro incubation with sporozoites. Not all antibody preparations that neutralize infection following direct incubation with sporozoites are able to reduce infection in mice when administered orally in combination with oocysts. Hence, this more rigorous oral challenge provides a preferable assay from which to draw conclusions about the functional value of a mAb and the importance of the epitope it defines.

Since mAb C6B6 and 7D10 recognized non-glycosylated amino acid epitopes, they were used by the present inventors to screen clones isolated from a cDNA library of C. parvum sporozoites. Identification of reactive clones provided the opportunity to sequence gene fragments encoding these neutralization-sensitive amino acid epitopes. The nucleotide sequence for a complete ORF was deduced from sequences of overlapping cDNAs. Because similar sized PCR products were generated from RNA and genomic DNA using 5' and 3' gene primers, this gene appears to lacl. introns, an observation consistent with reports that C. parvum genes cloned to date do not contain introns [Jones, D. E. et al., Molec. Biochem. Parasitol., 71, 143–147 (1995)].

Determination of the gene sequence was complicated by the occurrence of artifacts in clones C7 and C11. Three experimental results support the view that the non-consensus sequences of C7 and C11 became artifactually associated with p23 coding sequences during cloning. The first is that these sequences do not agree with consensus sequence of 10 other clones. The second is that primer pairs incorporating the consensus sequence generated PCR products from C. parvum RNA, genomic DNA and cDNA clones containing these primer sequences. In contrast, primer pairs that incorporated consensus C7 or C11 non-consensus sequences failed to generate PCR products from C. parvum RNA or genomic DNA, but did produce an expected PCR product from C7 or C11 plasmid, respectively. In addition, our unpublished results indicate that we have cloned two examples of the gene encoding the non-consensus C7 sequence, and it is distinct from the p23 consensus sequence. Taken together, these results strongly indicate that association of C7 and C11 non-consensus sequences with the p23 sequences resulted from cloning artifacts.

The predicted polypeptide has a molecular weight of 11.3 kDa, based on amino acid sequence, instead of approximately 23 kDa as determined by western blots of C. parvum proteins separated on polyacrylamide gels. This size discrepancy may be accounted for by physical properties of the protein, since the estimated $M_r$ for rC5 in FIG. 5 is approximately 21 kDa, whereas the predicted $M_r$ is 8.3 kDa (4.6 kDa encoded by the cDNA and 3.7 encoded by the β-galactosidase gene). Protein glycosylation might also account for differences in predicted versus apparent $M_r$, since there is evidence for glycosylation of C. parvum proteins, including p23 [Tilley et al., *Infect. Immun.* 59, 1002–1007 (1991); Luft et al., *Infect. Immun.* 55, 2436–2441 (1987); Petersen et al., *J. Protozool.* 38, 20S–21S (1991); Petersen et al., *Infect. Immun.* 60, 5132–5138 (1992)]. However, glycosylation would not explain the anomalous migration of rC5. Further characterization of p23 will be required to determine the cause of this size discrepancy. Nevertheless, evidence summarized below leads us to conclude that the protein encoded by the gene described herein represents the p23 polypeptide.

That the ORF sequence in FIG. 3 encodes the polypeptide component of p23 is shown by the following. Both mAb C6B6 and 7D10 identified a single protein band in *C. parvum* sporozoite isolates at 23 kDa, as did polyclonal serum raised to the C-terminal 29 amino acid polypeptide. Hexamer peptides synthesized from the predicted sequence and amino acid translation of the ORF allowed identification of a repeat linear epitope for mAb 7D10. The nucleotide sequence putatively encoding p23 and neutralization-sensitive epitopes was detected in *C. parvum* sporozoite RNA. In addition, we have detected the same nucleotide sequence in a clone from a *C. parvum* merozoite cDNA library (unpublished observations). This clone was identified by direct screening with mAb C6B6 and 7D10.

A linear epitope (QDKPAD; SEQ ID NO:9) was directly demonstrated for mAb 7D10, and has not been detected in previously-reported *C. parvum* sequences [Jones, D. E. et al., *Molec. Biochem. Parasitol.*, 71, 143–147 (1995); Lally, N. C. et al., *Molec. Biochem. Parasitol.*, 56, 69–78 (1992); Ranucci, L. et al., *Infect. Immun.*, 61, 2347–2356 (1993); Jenkins, M. C. et al., *Infect. Immun.*, 61, 2377–2382 (1993); Jenkins, M. C. and Fayer, R., *Molec. Biochem. Parasitol.*, 71, 149–152 (1995); Nelson, R. G. et al., *J. Protozool.*, 38, 52S–55S (1991); Gooze, L. et al., *J. Protozool.*, 38, 56S–58S (1991); Kim, K. et al., *Molec. Biochem. Parasitol.*, 50, 105–114 (1992); Dykstra, C. C. et al., *J. Protozool.*, 38, 76S–78S (1991); Khramstov, N. V. et al., *J. Euk. Microbiol.*, 42, 416–422 (1995); Steele, M. I. et al., *Infect. Immun.*, 63, 3840–3845 (1995)]. The epitope for mAb C6B6 was not determined. The C6B6 mAb bound to a 27 amino acid peptide (SEQ ID NO:4) synthesized from the predicted translation of the 3' end of the ORF. However, it did not bind to any linear hexamer sequence within the 27 amino acid peptide, nor did it bind to any of three overlapping 12-mer peptides (SEQ ID NOs:6–8) contained within the 27 amino acid sequence. We postulate the epitope is conformation-dependent, and speculate that proline groups within the 27 amino acid peptide provide an opportunity for peptide folding [Fasman, G. D. et al., *Biopolymers*, 29, 123–130 (1990)].

EXAMPLE 7

Immunization of Cows

Adult cows have been successfully immunized with recombinant C7 protein. Adult cows were first immunized with 100 μg of recombinant C7 protein (SEQ ID NO:12) in monophosphoryl lipid A trehalose dimycolate adjuvant (R-700, Ribi, Hamilton, Mont.). Each cow was immunized subcutaneously three times at two week intervals. Blood serum was collected and tested for antibodies, but no detectable antibody response was observed.

Subsequently, a different group of adult cows than the above was immunized with 300 μg of recombinant C7 protein (SEQ ID NO:12) in adjuvant (R-700, Ribi, Hamilton, Mont.). Each cow was immunized subcutaneously three times at two week intervals. Blood serum was collected and tested for antibodies; high titres of antibodies to the C7 peptide and to native p23 were detected. Additionally, colostrum was collected from the immunized cows; high titres of antibodies to the C7 peptide and to native p23 were detected in the colostrum.

The foregoing is illustrative of the present invention, and is not to be construed as limiting thereof. The invention is defined by the following claims, with equivalents of the claims to be included therein.

That which is claimed is:

1. An isolated protein comprising the amino acid sequence of SEQ ID NO:2.

2. The protein of claim 1, consisting of the amino acid sequence of SEQ ID NO:2.

3. An isolated peptide consisting of the amino acid sequence of SEQ ID NO:4.

4. An isolated peptide consisting of the amino acid sequence of SEQ ID NO:9.

5. An isolated peptide consisting of the amino acid sequence of SEQ ID NO:3.

6. An isolated peptide consisting of an amino acid sequence selected from the group consisting of the amino acid sequence of SEQ ID NO:11, the amino acid sequence of amino acids 77 to 187 of SEQ ID NO:12 and the amino acid sequence of SEQ ID NO:12.

7. A composition comprising the protein of claim 1 in a pharmaceutically acceptable carrier.

8. A composition comprising the peptide of claim 3 in a pharmaceutically acceptable carrier.

9. A composition comprising the peptide of claim 4 in a pharmaceutically acceptable carrier.

10. A composition comprising the peptide of claim 5 in a pharmaceutically acceptable carrier.

11. A composition comprising the protein of claim 1 in a pharmaceutically acceptable carrier.

12. A method of inducing an immune response in a subject, comprising administering an immunogenic amount of the peptide of claim 3 to the subject.

13. A method of inducing an immune response in a subject, comprising administering an immunogenic amount of the peptide of claim 4 to the subject.

14. A method of inducing an immune response in a subject, comprising administering an immunogenic amount of the peptide of claim 5 to the subject.

15. A method of inducing an immune response in a subject, comprising administering an immunogenic amount of the peptide of claim 6 to the subject.

16. A composition comprising the peptide of claim 6 in a pharmaceutically acceptable carrier.

* * * * *

UNITED STATES PATENT AND TRADEMARK OFFICE
CERTIFICATE OF CORRECTION

PATENT NO. : 6,759,048 B1
DATED : July 6, 2004
INVENTOR(S) : Perryman et al.

It is certified that error appears in the above-identified patent and that said Letters Patent is hereby corrected as shown below:

Title page,
Item [73], the third Assignee should read -- Washington State University Research Foundation --
Item [56], References Cited, U.S. PATENT DOCUMENTS, please add:

-- 6,110,463    8/2000    Riggs et al. --
OTHER PUBLICATIONS, please add:

Lumb et al. "Electrophoretic and Imminoblot Analysis of *Cryptosporidium* Oocysts" *Immunol. Cell. Biol.* 66:369-376 (1988)

Lumb et al. "Localization of a 23 000 MW Antigen of *Cryptosporidium* by Immunoelectron Microscopy" *Immunol. Cell Biol.* 67:267-270 (1989)

Répérant et al. "Major Antigens of *Cryptosporidium Parvum* Recognized by Serum Antibodies from Different Infected Animal Species and Man" *Veterinary Parasitology* 55:1-13 (1994)

Tilley et al. "*Cryptosporidium Parvum* (Apicomplexa: Cryptosporidiidae) Oocyst and Sporozoite Antigens Recognized by Bovine Colostral Antibodies" *Infection and Immunity* 58(9):2966-2971 (1990) --

Column 24,
Line 3, should read -- 11. A composition comprising the protein of claim 2 in a --

Signed and Sealed this

Twenty-first Day of December, 2004

JON W. DUDAS
*Director of the United States Patent and Trademark Office*